United States Patent [19]

Wilson et al.

[11] 4,334,535
[45] Jun. 15, 1982

[54] CONDUIT DEVICE FOR RAPID PRIMING AND FLOW OF LIQUID

[75] Inventors: David A. Wilson, Novato; Frank J. Serany, Danville, both of Calif.

[73] Assignee: Cutter Laboratories, Inc., Berkeley, Calif.

[21] Appl. No.: 177,700

[22] Filed: Aug. 12, 1980

[51] Int. Cl.³ .............................................. A61M 5/00
[52] U.S. Cl. .............................. 128/214 D; 128/272; 128/DIG. 24
[58] Field of Search ............ 128/214 R, 214.2, 214 B, 128/214 C, 214 D, 214 G, 227, 272, DIG. 26, DIG. 24

[56] References Cited

U.S. PATENT DOCUMENTS

| | | | |
|---|---|---|---|
| 2,884,924 | 5/1959 | Shaw | 128/214 C |
| 3,554,256 | 1/1971 | Anderson | 128/214 D |
| 3,756,237 | 9/1973 | Chittenden | 128/214 R X |
| 4,170,994 | 10/1979 | Komatsu | 128/214 D X |
| 4,173,223 | 11/1979 | Raines | 128/214 C |
| 4,191,183 | 3/1980 | Mendelson | 128/214 C X |
| 4,257,416 | 3/1981 | Prager | 128/214 |

Primary Examiner—Stephen C. Pellegrino
Attorney, Agent, or Firm—Robert E. Allen

[57] ABSTRACT

A unit for rapid priming and flow of liquid through the unit is disclosed. The unit comprises a connector for communicating with liquid in a sealed container, the connector having an exit orifice around which is secured one end of a primer tube. The other end of the primer tube is joined to a pooling conduit. The diameter of the primer tube is greater than the diameter of a drop of liquid released from the orifice and the diameter of the pooling conduit is no greater and preferably slightly less than the diameter of the drop of liquid. Multiple units can be joined to a common tube of enlarged diameter which leads into a pooling and dispensing container.

22 Claims, 5 Drawing Figures

U.S. Patent    Jun. 15, 1982    Sheet 1 of 2    4,334,535
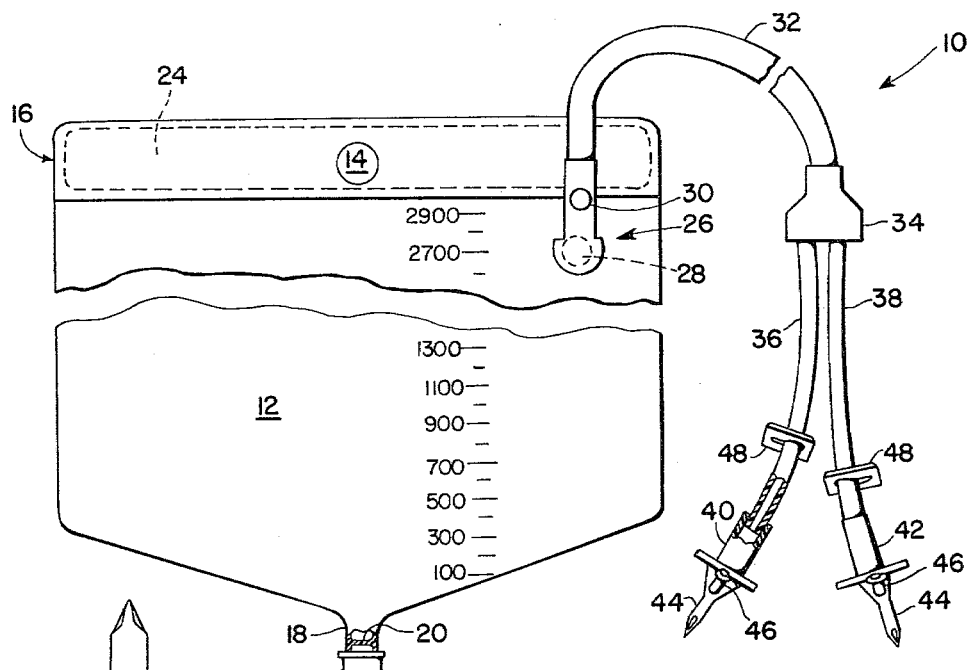
FIG. 1
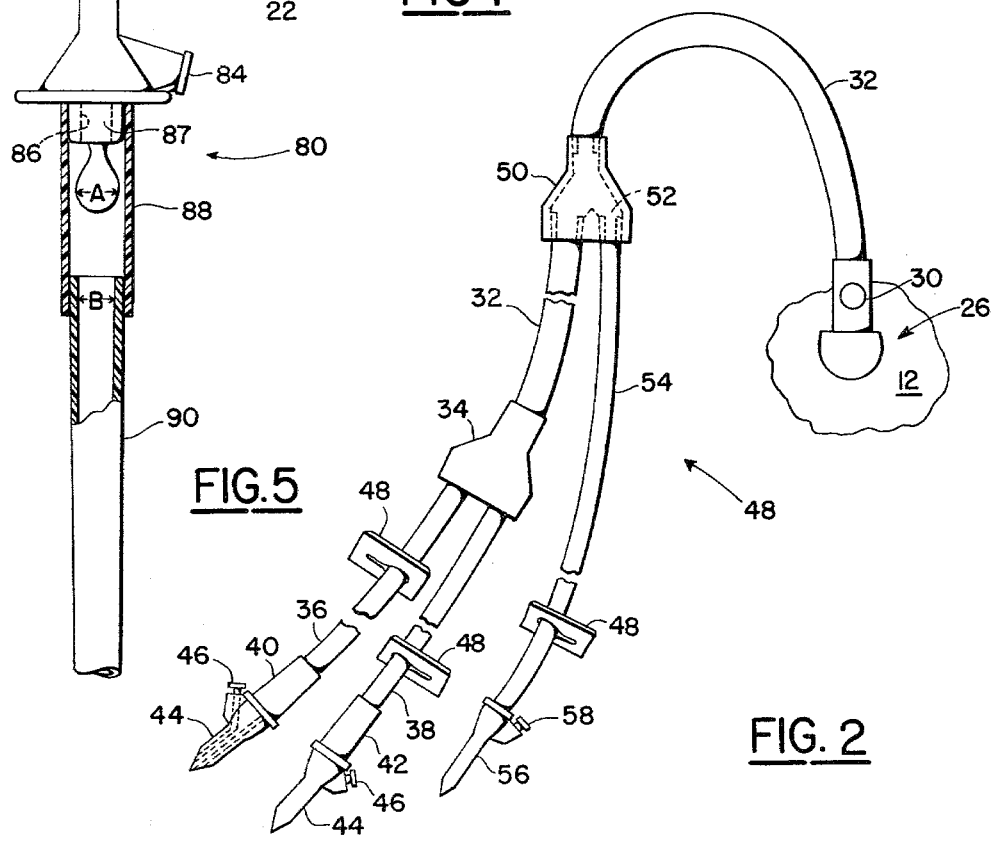
FIG. 5
FIG. 2

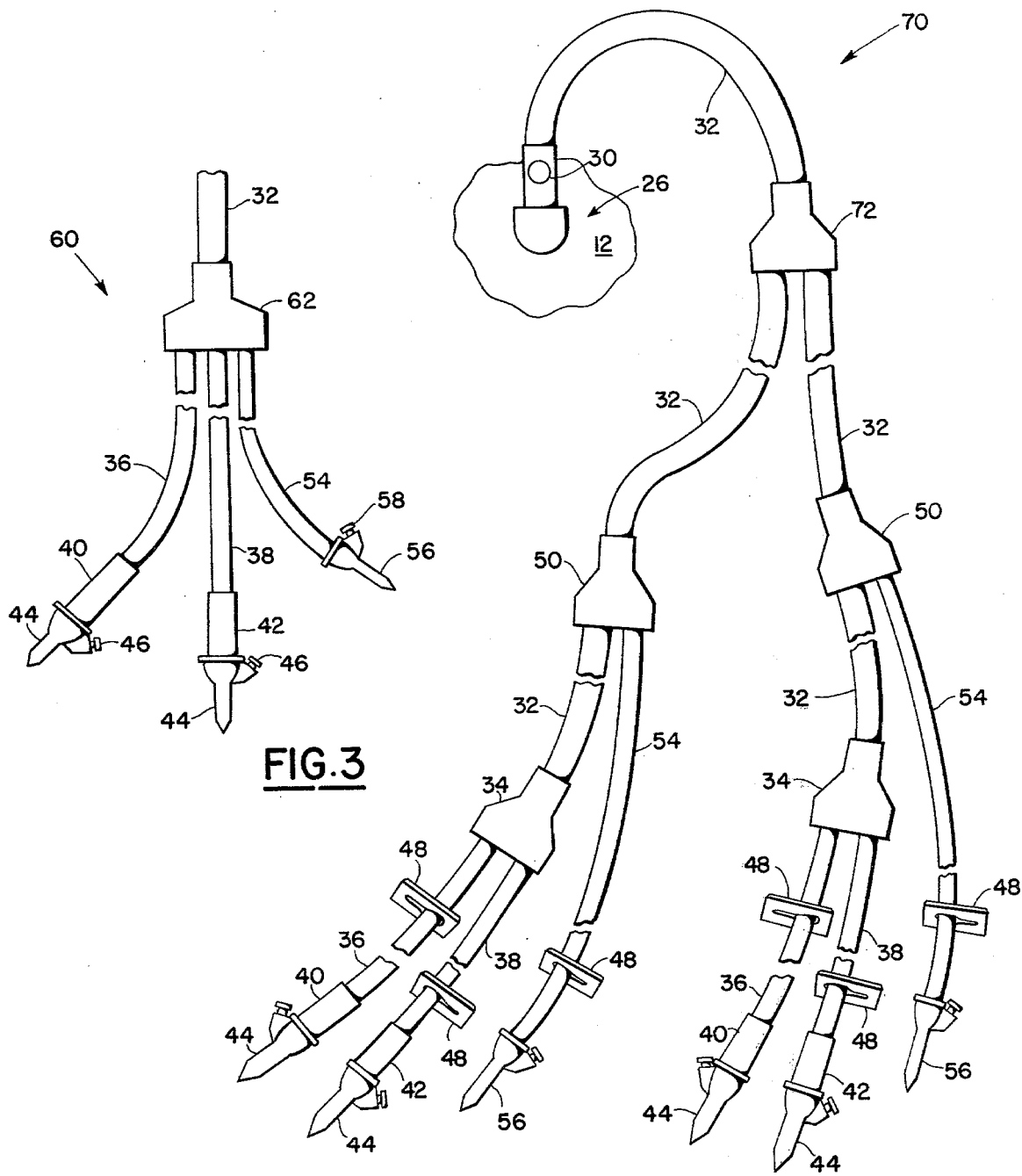

CONDUIT DEVICE FOR RAPID PRIMING AND FLOW OF LIQUID

BACKGROUND OF THE INVENTION

1. Field

This invention relates to a liquid delivery apparatus susceptible for rapid priming and rapid flow of liquids through the apparatus.

2. Prior Art

The are situations where it is desired to be able to transfer liquids rapidly by gravity flow from a container through a conduit and into a collecting container or cavity. For example, it is often desireable to administer simultaneously solutions of amino acids, carbohydrate, and fats to patients by the intravenous (I.V.) route to provide total nutritional needs. In current practice, a hospital pharmacist will add 500 ml. from a bottle of dextrose solution to a liter bottle containing 500 ml. of a solution of amino acids, conducting this operation using aseptic technique in a laminar air flow hood. Vitamins and essential minerals may be added to the mixture. The mixture is then transported to the patient for intravenous administration. A nurse may then introduce a fat emulsion into the administration set to mix with the amino acid-dextrose mixture as it flows through the set to the patient. This procedure must be repeated generally every eight to twelve hours and is time consuming for both nursing and pharmacy personnel.

A large volume flexible pooling container is commercially available for collecting by gravity and mixing distinct nutritional solutions stored in separate smaller containers to provide for a 24 hour supply. The large pooling container is in the form of a bag having at one end a slot for suspending the bag in a vertical position and at the opposite end two sealed inlet ports and a length of I.V. tubing with an inner diameter of about 0.11 inch. The tubing is connected to a Y-adaptor from which extends two shorter lengths of the same size tubing each of which is joined to a pointed cannula. To fill the pooling container for a 24 hour supply, the pharmacist inserts one of the cannulas into a bottle of amino acid solution and the other cannula into a container of dextrose solution, 50% for example, each containing 500 ml. of solution. The containers are suspended, clamps on the tubing are released and the solutions then flow into the pooling bag. After the containers are emptied, the cannulas are removed and reinserted into two more containers of solution and drained into the pooling bag. This process is repeated until the bag is filled with a day's supply of solution. In addition to the attention that must be given to see when the contents of two containers have been drained so that two more containers of solution can be installed for drainage, the time lapse for filling a three liter bag, for example, is on the order of about 21 minutes. The entire operation also should be conducted in a laminar air flow hood to reduce the chance for contamination since the cannulas are exposed to the environment each time they are withdrawn and reinserted. After the bag has been filled, the pooling tubing near the inlet into the bag is clamped and the remainder of the pooling tubing is severed. The pooled contents are then delivered to the patient where a nurse arranges it for I.V. administration by entry into one of the sealed ports. An additive solution such as insulin or one having a relatively high specific gravity, can be introduced into the bag through the other sealed port. However, unless the contents of the bag are thoroughly mixed, after such an introduction, there is a tendency for the additive to settle around the port leading from the bag so that the patient would receive the medication in concentrated form. This could have serious consequences.

SUMMARY OF THE INVENTION

The present invention relates to a priming and pooling or dispensing set which allows for rapid priming and rapid delivery of liquid through the set from a container of that liquid. The set comprises a hollow connector for joining the set to a container of liquid and for flow of the liquid therethrough, the outer end of the connector having an orifice around which and spaced therefrom is attached at its proximal end a primer tube whose inner diameter is greater than the diameter of a drop of liquid released from the orifice of the connector. Attached to the distal end of the primer tube is a dispensing or pooling conduit having a length substantially greater than that of the primer tube, the pooling conduit having an inner diameter no greater and preferably slightly less than the diameter of the drop of liquid released from the orifice of the connector. A set designed according to these requirements will allow liquid dropping from the orifice to form a solid column of that liquid at the top of the pooling conduit when the set is arranged in a vertical manner and with increasing length of this column, liquid is drawn through the orifice at an ever increasing rate so that the set quickly becomes primed and flow of the liquid through the set proceeds at a rapid rate. The set in its simplest embodiment as described above would have a number of important uses, particularly in the dispensing of viscous solutions. It would also find utility in the medical field, for example, in filling the peritoneal cavity with dialysis solution in those patients requiring this form of dialysis.

A further adaptation of this invention particularly useful in the medical area is in the situation where a physician prescribes a mixture of different solutions for parenteral administration to his patients, i.e., an extemporaneously compounded mixture designed to meet the specific needs of a particular patient. A set employing the principles of this invention which may include a flexible pooling and dispensing container of enlarged capacity allows for rapid priming and rapid pooling of these different solutions even under less than ideal conditions into the one large container, sufficient for a complete full day's supply.

A pooling and dispensing container set for this purpose comprises a large flexible bag with means for vertical suspension at one end and a dispensing port at the opposite end. The bag has an inlet port preferably located at the upper portion of the bag to which is connected tubing with an enlarged inner diameter. The outer end of the enlarged tubing is joined to an adaptor having at least two communicating channels each of which connects to a pooling conduit having an intermediate sized inner diameter. The other end of at least one of the pooling conduits is joined to a relatively short length of a primer tube having an inner diameter larger than that of the pooling conduit. The other end of the primer tube is attached to a hollow piercing member and surrounds the exit orifice of that member. In general the outside diameter of piercing members used in conventional parenteral solution administration sets is limited to a size which will readily penetrate the stopper on a 500 ml. or 1 liter bottle. The relatively small size of the opening at the piercing end, as well as the exit orifice, places a limitation on the rate of flow possible through the piercing member. Of course, the use of a larger piercing member would allow for greater flow but it would be impractical to have a manufacturer supply and a hospital to carry separate inventories on sets having different sizes in piercing members. It would also require separate inventories of bottles of the same kind of solution, one whose stoppers would accommodate smaller piercing members and another whose stoppers would accommodate larger piercing members. Consequently, the piercing members in the pooling sets of this invention conform generally to those currently in use for intravenous administration of parenteral fluids.

The pooling and dispensing container sets of the present invention often would be needed for a mixture of an amino acids solution, and a solution of a carbohydrate, such as 10% to 50% or even 70% dextrose. Solutions with high viscosity such as 50% and 70% dextrose flow very slowly through small bore tubing such as that used in conventional I.V. sets. The inner diameters of such sets are generally in the range of about 0.09 to about 0.12 inch. Consequently, the sets of the present invention when used in this situation are equipped with pooling conduits having inner diameters greater than about 0.14 inch but no greater and preferably slightly smaller than the diameter of the drops of liquid which are released from the orifice of the piercing member. One of the preferred size of pooling conduits is that having an inner diameter of about 0.19 inch.

Priming of a set is that condition wherein all the tubing below the orifice, i.e., the pooling conduits and enlarged connecting tubing leading up to the pooling bag, is totally filled with an unbroken column of liquid, at which point a maximum steady state of flow rate can be achieved.

A primer tube between the piercing member and pooling conduit is critical for rapid priming of a set with viscous solutions. If the pooling conudit were connected directly to the piercing member, the first drop of viscous liquid released from the orifice almost invariably makes complete contact with the wall of the conduit. In doing so the high surface tension of the viscous liquid, more often than not, will cause the drop to remain in place and not move down the conduit. Priming becomes most difficult and prolonged since some external manipulation must usually be made on the set to force the solution through the conduit to the point where a solid column of liquid of sufficient length is formed to pull more liquid through the orifice.

When solutions of low viscosity, such as an I.V. fat emulsion, are to be transferred into the pooling bag, high surface tension at the pooling conduit and orifice interface is not a problem generally, hence a primer tube is not usually necessary between the orifice and the pooling conduit.

A pooling and dispensing container set can have any number of individual piercing member-pooling conduit units, with or without primer tubes. The units are connected by adaptors which bring together liquids flowing from each individual unit into the common enlarged diameter tubing connected to the bag. One such arrangement with six units is particularly useful for the most rapid pooling of two bottles each of amino acids, dextrose and fat emulsion into the dispensing bag. This mixture would then provide a full day's supply of solution for total parenteral nutrition therapy in an individual patient.

Amino acids, dextrose, and fat emulsion solutions are often supplied in containers which do not have an air-inletting mechanism. Air must be allowed to enter the bottle in order for the contents to drain from that bottle. To accomodate this situation, the piercing member of the sets of this invention includes an air-inletting passage with a bacterial filter.

Ordinarily, one would imagine that in order to prime and drain liquids through a set as rapidly as possible, it would only be necessary to use tubing with a very large diameter. This tubing could be connected to a piercing member at one end and to a pooling bag at the other end. However, when a set was constructed thusly, it was noted that liquid dropping from the orifice would merely trickle down the enlarged tubing. The tubing would never become primed, i.e., a solid column of liquid could not be formed and no head pressure could be developed. Consequently, delivery time of the liquid through the tubing was extremely prolonged.

A set was constructed with small diameter tubing of a size currently in use for I.V. administration sets, i.e., tubing with an inner diameter of about 0.12 inch. This tubing was connected to the orifice of a piercing member whose diameter was larger than that of the tubing. Priming times were rapid but the delivery times were quite prolonged, particularly with viscous solutions. The prolonged delivery time was determined to be a consequence of adhesion of the liquid to the wall as well as the restricting size of the lumen of the tubing.

By using tubing of intermediate size, about 0.19 inch inner diameter, the orifice produced drops with about the same diameter as that of the tubing, flow rate through the tubing was rapid once priming had been established. However, with viscous solutions, surface tension often held the initial drop to the sides of the tubing wall at the tubing-orifice interface and prevented the liquid from flowing down the tubing. This is particularly noticed with tubing having a hydrophobic surface.

The use of a priming and delivery set constructed according to the principles of this invention has overcome these aforementioned problems of slow and difficult priming or slow delivery particularly with liquids of high viscosity. It is believed that with the diameter of the primer tube being larger than the diameter of the drop of liquid released from the orifice, the first drop or drops which reach the impeding or stepped-down edge of the pooling conduit will form a small solid column of liquid. Subsequent drops from the orifice fall substantially free and will strike the top of the column of liquid imparting kinetic energy. Such energy will break the adhesion of liquid to the walls of the pooling conduit to allow an ever increasing column of liquid to descend. As the length of the column increases, a greater head pressure is developed which helps to pull liquid through the orifice at an increasing rate. Priming rates are thus rapidly achieved even with viscous liquids and rapid flow rates through the pooling conduit are possible since the size of the conduit is not materially restricting.

A further understanding of the invention can be developed from the detailed description of certain embodiments which follow.

BRIEF DESCRIPTION OF THE DRAWINGS

FIG. 1 is an elevational view of a pooling and dispensing container set in accordance with the principles of the invention, showing two pooling conduits;

FIG. 2 shows an embodiment relating to the set of FIG. 1, illustrating only the pooling conduit portions of the set, in this case there being three pooling conduits;

FIG. 3 shows a modification of the set of FIG. 2;

FIG. 4 shows still another modification of the set of FIG. 1, there being six pooling conduits; and FIG. 5 illustrates a portion of a primer-dispensing set, partly in cross-section, according to the principles of the invention.

DETAILED DESCRIPTION OF PREFERRED EMBODIMENTS

A pooling and dispensing container set 10 as shown in FIG. 1 comprises an enlarged flexible bag 12, for example, one having a capacity for 3 liters of solution, with a slot 14 at the top portion 16 for hanging the bag vertically on a hook (not shown), and an outlet port 18 having a pierceable membrane 20 closing port 18. The neck of port 18 may also be enclosed by a removable cap member 22 to maintain sterility prior to use. Bag 12 may be formed by heat sealing two sheets of plastic material around the periphery and the top 16 may be strengthened by the inclusion of a rigid member 24 sealed between the two sheets.

An inlet port 26 is secured to one wall near the top of bag 12 to communicate with an aperture 28 in the bag wall. The inlet port 26 may have a resealable additive port 30 through which additive solutions can be introduced into bag 12. Additive port 30 can be located elsewhere in direct communication with the interior of the bag but preferably positioned either on inlet port 26 or at a location remote from the outlet port 18 so as to avoid concentrating the additive solution near the outlet port and prevent its entering the patient in concentrated form.

Joined to inlet port 26 is a length of tubing 32 having an enlarged internal diameter, in this embodiment, for example, the internal diameter is preferably about 0.25 inch. Larger or smaller diameters are acceptable as long as flow of liquid through it is not unduly restricted when smaller diameter tubing is used. The outer end of tubing 32 is connected to an adaptor 34 from which extend two pooling conduits 36 and 38 whose inner diameters (I.D.) are of intermediate size, less than that of tubing 32 but larger than that of tubing in conventional I.V. sets which normally have tubing with an I.D. of about 0.10 inch. In this particular embodiment of the I.D. of the pooling conduits 36 and 38 is about 0.19 inch. Again they should be of a size which results in very little restriction to flow of liquids through them. It is preferred that the sum of the cross-sectional areas of conduits 36 and 38 should approximate the cross-sectional area of tubing 32.

Joined to the outer ends of conduits 36 and 38 are short sections of primer tubes 40 and 42 whose internal diameters are larger than those of conduits 36 and 38. In this embodiment their internal diameters are about 0.25 inch. The length of primer tubes 40 or 42 is not critical but preferably the length is not much greater than 2 or 3 inches and can be less without compromising the disfunction of rapid priming and rapid flow through the interconnected tubes and conduits. The outer ends of primer tubes 40 and 42 are connected to the outflow orifice of a hollow piercing member 44, the orifice diameter being less than the diameter of tubes 40 or 42. Piercing member 44 is designed to penetrate a closure on a bottle or container of a solution such as amino acids, dextrose, or the like. The piercing member should have an air-inletting passage 46, preferably with a bacterial filter, for the transfer of solutions from rigid containers which do not otherwise have a separate air-inletting capability.

Another embodiment relating to the pooling and dispensing container set of FIG. 1 is shown in FIG. 2. In this embodiment 48, a hollow adaptor or connector 50 similar to adaptor 34 is located between adaptor 34 and inlet port 26. Connector 50 has a through passage which interconnects the segments of tubing 32 and also a connecting passage 52 which communicates with a segment of a pooling conduit 54, the internal diameter of which can be the same or approximately that of conduits 36 and 38. The outer end of conduit 54 is attached to a piercing member 56 directly or it can be separated from the piercing member by a short length of primer tube (not shown), similar to primer tubes 40 or 42. The pooling conduit 54 with its piercing member 56 is intended for entry into and delivery of a third liquid from its container, as for example a fat emulsion, which differs from two other liquids such as amino acids and dextrose solutions for example, which are delivered through the two pooling conduits leading into adaptor 34. When a fat emulsion is to be delivered, an air-inletting passage 58, preferably with a bacterial filter, should also have a check valve in the passage to prevent blockage of air through the filter which could occur if the fat emulsion were to contact the filter. Check valves in airway passages of piercing members are well known in the art and need not be detailed here.

As an alternative to the embodiment of the set shown in FIG. 2, the set can be modified as illustrated in FIG. 3. In this modification 60, the enlarged tubing 32 leading from inlet port 26 of bag 12 is connected to a three-inlet adaptor 62 to which are joined three segments of pooling conduits 36, 38 and 54. The rest of the components, i.e., primer tubes and piercing members are the same or similar to those described supra.

If one wishes to collect more than two or three volumes of solutions simultaneously into bag 12, embodiment 70 as shown in FIG. 4 is illustrative of a set capable of pooling up to six solutions at one time without resorting to a disconnect and reconnect procedure which would be necessary if the contents of more than three containers were pooled into bag 12 using the sets of FIGS. 1 through 3. In essence, set 70 connects two triple pooling units such as the unit shown in FIG. 2 to a connector 72. Although not shown specifically in FIG. 4, set 70 could be further modified whereby primer tubes such as tubes 40 or 42 are interposed between both piercing members 56 and pooling conduits 54. Obviously, two pooling units such as that shown in FIG. 3 could be connected to connector 72 to achieve a similar type of set.

FIG. 5 shows in greater detail the features of the present invention, not only in terms of how it applies to the various embodiments of pooling and dispensing sets disclosed above, but also as it can apply to any situation where it is desired to achieve rapid priming and rapid dispensing of a liquid from a container through a dispensing set under conditions of gravity flow. A dispensing set 80 comprises a connector means 82 for providing liquid flow communication with the liquid in a container (not shown); in this case it is a conventional hollow pointed cannula which can have a filtered air-inletting passage 84. The cannula has a drip tube 86 defining an exit orifice 87 for liquids as shown in dotted lines. A primer tube 88 surrounds orifice 87 and the inner diameter of primer tube 88 should be at least large enough that a drop of liquid released from orifice 87 will either fall free or will make contact with only a portion of the circumference of the inner wall of tube 88. A dispensing conduit 90, its upper end secured within the lower end of primer tube 88, should have an inner diameter B which is substantially no greater than the diameter A of the drop of liquid so that the complete circumference of the inner wall of conduit 90 makes contact with the drop. The inner diameter of conduit 90 should be as large as possible, consistent with the above-stated requirement, so that the size of the conduit does not cause significant restriction to the flow of liquid through it. In the situation where this connector-primer tube-dispensing conduit unit is used in a set of the types disclosed in FIGS. 1-4, dispensing conduit 90 should have an inner diameter greater than about 0.14 inch.

The pooling and dispensing container sets as disclosed in FIGS. 1-4 are most useful in the medical area, particularly where a physician wishes to have "extemporaneously compounded" a specific composition of various ingredients for prolonged intravenous administration to a patient. In the case where he might wish to have a mixture of amino acids and glucose sufficient for a full day's administration, a pharmacist using the set of FIG. 1 would lay bag 12 on a flat surface, preferably in a laminar air flow hood. He would then insert one piercing member 44 through the stopper of a bottle of amino acids solution and the other piercing member 44 through the stopper of a bottle of dextrose solution. The two bottles are suspended, generally at least about 18 inches above bag 12, and clamps 48 (which were previously closing pooling conduits 36 and 38) are moved to the open position. Initially a few drops of either solution will collect and form a small solid column of liquid at the top of the pooling conduits. This column also extends partly into the primer tubes. As the column of liquid grows it is pulled downward by the force of gravity which in turn pulls more liquid through the orifices of the piercing members with ever increasing speed. A solid column of liquid is quickly formed throughout the pooling conduits and enlarged tubing 32 (priming period) and the contents of the two suspended bottles very rapidly drains into bag 12. The same process is repeated twice with additional bottles of amino acids and dextrose solutions until bag 12 becomes filled with the desired quantity of the mixed solutions, generally three liters or less. Tubing 32 is either heat-sealed closed or hermetically clamped near inlet port 26 and then severed above the sealed or clamped area. Additives such as vitamins and minerals can be introduced through additive port 30, if desired, where they become well dispersed throughout the solution in the bag. Bag 12 is then transported to the patient and suspended. Connection with an I.V. administration set through outlet port 18 is made for delivery of a full day's supply of the nutritional solution to the patient. The entire procedure for gravity filling bag 12 can be performed in about 8 minutes 25 compared to about 20 minutes to gravity fill the current commercially available pooling and dispensing container set, using 50% dextrose as the carbohydrate solution, for example.

The sets of FIG. 2 or FIG. 3 can be used for pooling three different solutions and are particularly adapted for the pooling of a day's supply of solutions for total parenteral nutrition, i.e., amino acids, carbohydrates and fats. Entry into bottles of amino acids solution and dextrose solution are made with the two piercing members 44 and a bottle of a fat emulsion is entered by piercing member 56. The process of pooling an 8% solution of amino acids, a 50% solution of dextrose, and a 10% fat emulsion (500 ml. each), with the bottles suspended about 15-20 inches above bag 12, requires about four minutes. Repeating the pooling of three more bottles of these solutions so as to collect a 24 hour supply requires a total pooling time of about ten minutes.

The set of FIG. 4 can be used for pooling as much as six different solutions. Preferably, it is used for pooling the contents of two 500 ml. bottles each of amino acids, dextrose and fat emulsion simultaneously for use over a 24 hour period. The procedure for accomplishing this requires only about seven minutes and has the further advantage that the procedure does not require the use of a laminar air flow hood since the piercing members are used but once.

The set of FIG. 5 can be used in any situation where one wishes to drain rapidly by gravity a liquid from a container into another receptacle, a body cavity, or the like. For example, set 80 would be useful in draining dialysis solutions from a container into the peritoneal cavity of patients requiring this type of dialysis. In this situation, the outer end of dispensing conduit 90 would have a suitable adaptor for connection to an appropriate catheter positioned through the abdominal wall and into the peritoneal cavity.

Various modifications of the several embodiments of sets as disclosed above will become apparent and this invention is intended to include such modifications and to be limited only by the scope of the claims.

We claim:

1. A pooling and dispensing container set for parenteral solutions having an inlet port and an outlet port, the outlet port having closure means adapted for being opened by a cannula on a parenteral solution administration set, the inlet port being connected to a pooling system comprising a length of enlarged inner diameter tubing one end of which is connected to the inlet port and the other end being connected to an adaptor having a first and a second inlet, first and second pooling conduits each connected at its one end to the first and second inlets, respectively, the inner diameters of the pooling conduits being smaller than the inner diameter of the enlarged tubing, the other ends of the pooling conduits each being joined to a first and a second primer tube, respectively, each primer tube being connected at its outer end to a hollow coupler having means at one end for entry into a container of parenteral solution and an exit orifice at the other end, the primer tube surrounding the orifice and having an inner diameter larger than the diameter of a drop of the solution released from the orifice, the inner diameter of the pooling conduit being smaller than the inner diameter of the primer tube and at least no greater than the diameter of the drop of solution.

2. The set of claim 1 wherein the couplers include a through passage for solutions and an air-inletting passage equipped with a bacterial filter.

3. The set of claim 1 further including clamping means associated with at least one of the pooling conduits.

4. The set of claim 1 wherein the outlet port is located at one end of the container and the inlet port is located at a position remote from the outlet port.

5. The set of claim 1 wherein the set includes an additive port closed by a resealable closure.

6. The set of claim 5 wherein the additive port is located on the inlet port.

7. The set of claim 1 wherein the enlarged tubing further includes a first hollow connector located at an intermediate position in the enlarged tubing between the adaptor and the inlet port, the connector having a passageway in communication with the enlarged tubing and with a third pooling conduit with a third hollow coupler attached at the outer end of the third pooling conduit, the inner diameter of the third pooling conduit being substantially the same as those of the first and second pooling conduits.

8. The set of claim 7 wherein a third primer tube is interposed between the outer end of the third pooling conduit and the third coupler.

9. The set of claim 7 wherein the enlarged tubing further includes a second hollow connector located between the first connector and the inlet port, the second connector having a passageway in communication with the enlarged tubing, a second section of enlarged inner diameter tubing connected to an inlet passage communicating with the passageway of the second connector at one end and connected to a third connector at the other end, the third connector having a first and a second inlet, each of the inlets communicating with first and second pooling conduits, respectively, and having inner diameters smaller than the inner diameter of the second section of enlarged tubing, the outer ends of the pooling conduits each being joined to a first and a second primer tube, respectively, and with a hollow coupler joined to the outer end of each of the pooling conduits, the inner diameters of the primer tubes being larger than the inner diameters of the pooling conduits.

10. The set of claim 9 further including a fourth hollow connector located at an intermediate position in the second length of enlarged tubing and having a passageway in communication with the second length of enlarged tubing and with a third pooling conduit, the outer end of the third pooling conduit being connected to a hollow coupler, the inner diameter of the third pooling conduit being substantially the same as those of the first and second pooling conduits.

11. The set of claim 10 wherein the couplers include a through passage for solutions and an air-inletting passage equipped with a bacterial filter.

12. The set of claim 1 or 10 wherein the ratio of the inner diameter of the primer tubes to the inner diameter of the respective pooling conduits is about 1.3 to 1.

13. The set of claim 1 or 10 wherein the primer tubes are substantially no longer than about three inches.

14. The set of claim 1 wherein the adaptor further includes a third inlet to which is joined a third pooling conduit the outer end of which is in communication with a hollow coupler.

15. The set of claim 14 wherein a third primer tube is interposed between the third pooling conduit and the coupler.

16. A set for connecting to a container of liquid for rapid priming and dispensing of the liquid through the set by gravity flow comprising connector means for communicating with the liquid in the container, the connector means having an outflow orifice, a primer tube joined to the connector means and surrounding the orifice, and a dispensing conduit connected to the outer end of the primer tube, the inner diameter of the primer tube being of a diameter only greater than a diameter of a drop of the liquid when released from the orifice to the extent that said drop makes partial but less than complete circumferential contact with the wall of the primer tube, the cross-sectional area of the dispensing conduit being less than the cross-sectional area of the primer tube and no greater than the cross-sectional area of the drop of liquid released from the orifice, and at least a portion of the length of the dispensing conduit being substantially greater than the length of the primer tube when the set is arranged in a vertical manner, the dispensing conduit having an inner diameter greater than 0.10 inch.

17. The set of claim 16 wherein the connector means comprises a hollow piercing member suitable for penetrating a closure on a container.

18. The set of claim 17 wherein the piercing member includes a through passage for liquid flow from the container and an air-inletting passage.

19. Pooling and dispensing apparatus for parenteral solutions, comprising:
 (a) a flexible pooling bag having a hanger at an upper portion and a closure at a lower portion, said closure comprising a pierceable diaphragm for use with an administration set for emptying the bag;
 (b) an inlet portion, for filling said bag with more than one solution, communicating at one end with said upper portion of said bag;
 (c) a plurality of pooling conduits extending in length from said inlet portion for connection to a container, at least one of which pooling conduits is coupled to a primer tube;
 (d) said primer tube extending from an end opening of said pooling conduit and communicating with a hollow connector having an inner diameter orifice and means at one end for entry into a container,
 (e) said primer tube having an inner diameter greater than the inner diameter of said pooling conduit and the inner diameter of said hollow connector so that initial drops of solution from said container passing through said hollow connector pass through said pooling conduit to establish a moving column of solution on priming, said moving column of solution filling said primer tube upon completion of priming.

20. The apparatus of claim 19 wherein the ratio of the inner diameter of the primer tube to the inner diameter of the pooling conduit is about 1.3 to 1.

21. The apparatus of claim 19 or 20 further comprising a second primer tube, substantially identical to a first primer tube, extending from an end opening of a second pooling conduit.

22. The apparatus of claim 19 wherein said primer tube consists essentially of a flexible tube fit over an outer diameter of said hollow connector; and said pooling conduit consists at one end, essentially of a flexible tube fit internally into an inner diameter of said primer tube.

* * * * *